United States Patent [19]

Etherington

[11] Patent Number: 4,660,569

[45] Date of Patent: Apr. 28, 1987

[54] VENTING, AUTOMATIC-STOPPING, ASPIRATING PLUNGERS FOR SYRINGES

[75] Inventor: Roger F. Etherington, Newport Beach, Calif.

[73] Assignee: Sealsyringe Corporation, San Diego, Calif.

[21] Appl. No.: 827,516

[22] Filed: Feb. 10, 1986

[51] Int. Cl.$^4$ .............................................. A61B 5/00
[52] U.S. Cl. .................................... 128/765; 604/190
[58] Field of Search ............... 128/765, 766; 604/190, 604/218, 222, 405, 406, 187

[56] References Cited

U.S. PATENT DOCUMENTS

| | | | |
|---|---|---|---|
| 4,327,745 | 5/1982 | Ford, Jr. | 128/765 |
| 4,361,155 | 11/1982 | Anastasio | 128/765 |
| 4,373,535 | 2/1983 | Martell | 128/765 |
| 4,572,210 | 2/1986 | McKinnon | 604/190 X |

Primary Examiner—John D. Yasko
Attorney, Agent, or Firm—William F. Frank

[57] ABSTRACT

The present invention is a syringe plunger stem with band-like sealing means on one end and fingergrip means on the opposite end and being slidably and sealably insertable into the body of a syringe to variate the volume capacity of the chamber of said syringe. In the plunger there is a capillary action view-tube, positioned in constant sealing contact with the said band-like sealing means and extending longitudinally towards said fingergrip end of said plunger. Further, an air-permeable, liquid impervious porous material is positioned in the said capillary action view-tube that is nearest the said fingergrip end of the plunger. The said capillary action view-tube communicating with and positioned between the said chamber of said syringe and the said air-permeable, liquid impervious porous material. The present invention may also provide a secondary chamber area in the plunger.

15 Claims, 11 Drawing Figures

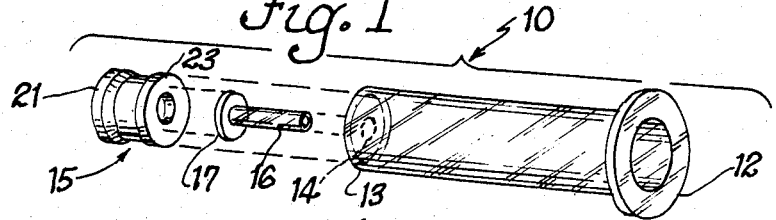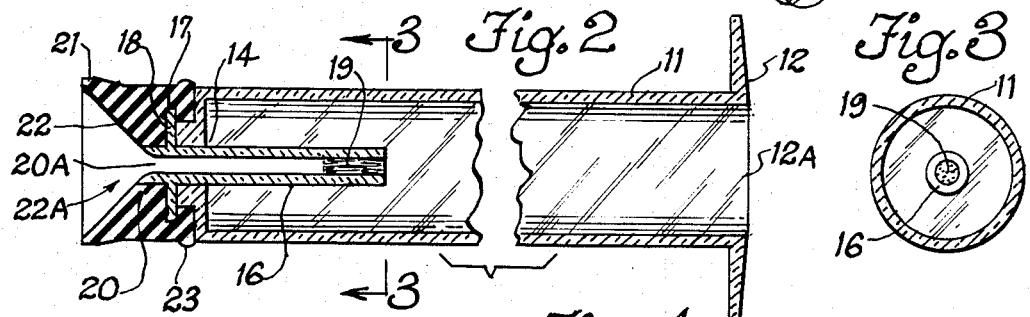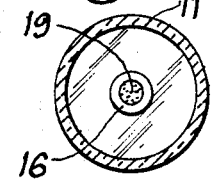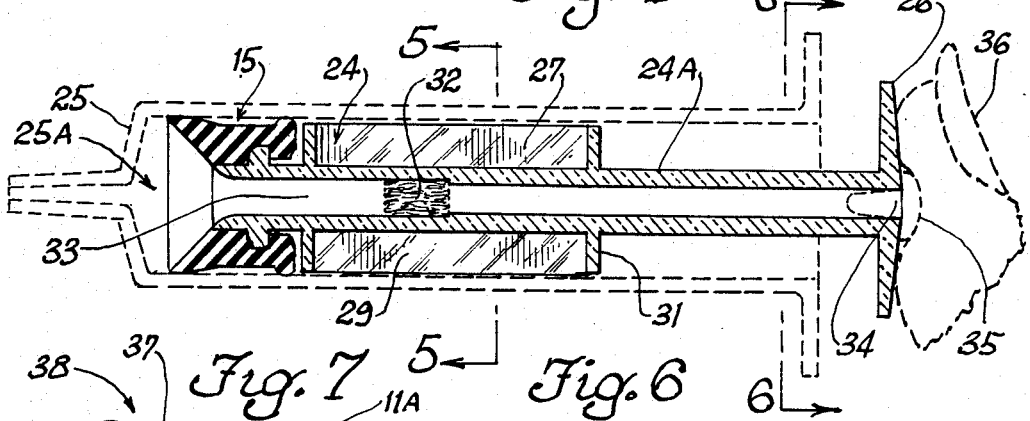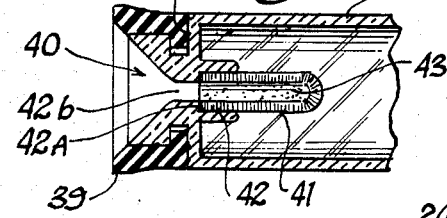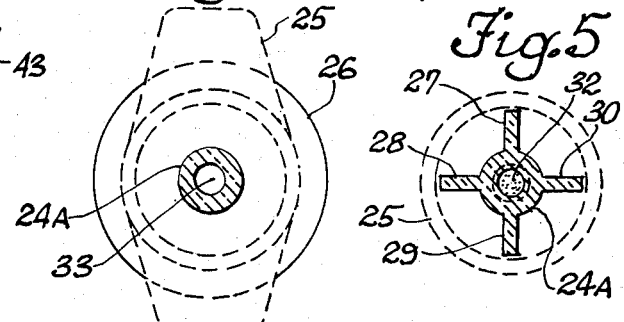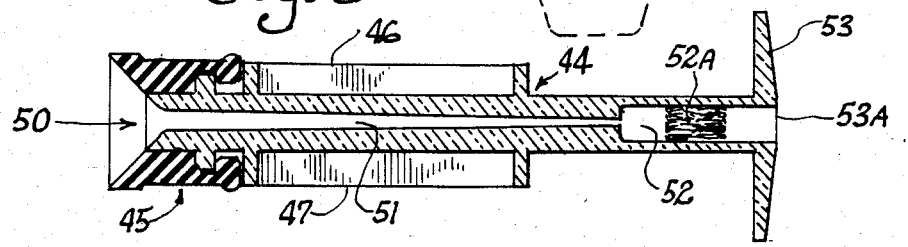

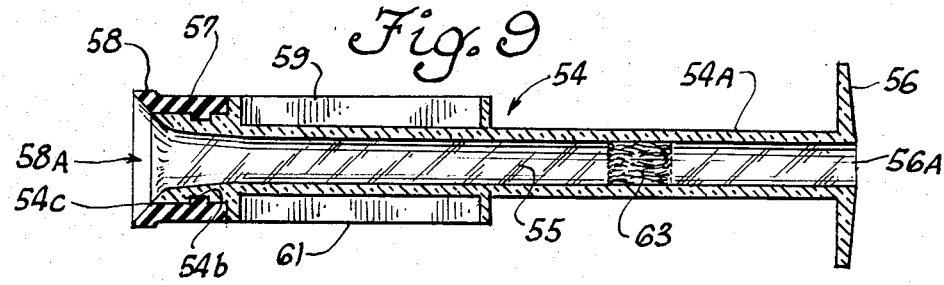
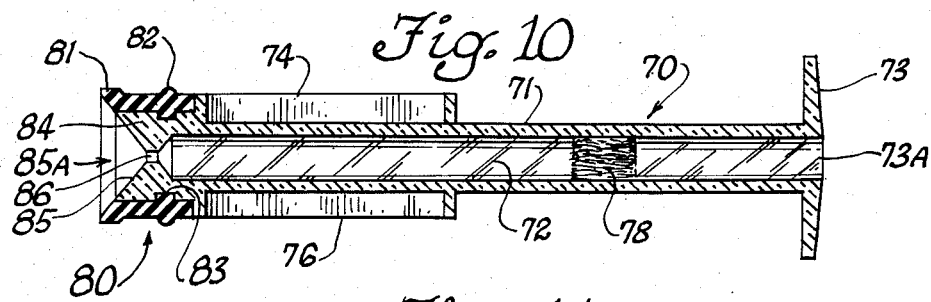
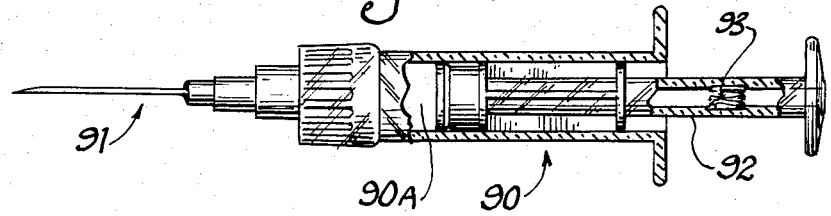

VENTING, AUTOMATIC-STOPPING, ASPIRATING PLUNGERS FOR SYRINGES

FIELD OF THE INVENTION

The present invention is in the field of syringes which are used to collect arterial blood samples from patients for blood gas analysis, and more particularly, to air-venting, automatic-closing, aspirating plungers that are used in the syringes for collecting arterial blood gas samples.

BACKGROUND OF THE INVENTION AND PRIOR ART

Syringes with air-venting, automatic-stopping, aspirating plungers, hereinafter referred to as vented plungers, are typically used for collecting arterial blood gas samples. Such syringes generally utilize a dry form of heparin (anti-coagulant) for preserving the collected blood sample. Since the dry heparin occupys only a small portion of the space in the chamber of the syringe, the remainder of the space between the plunger end and the end of the syringe body is filled with air. The desired objective is for all of the air in the syringe body to be forced through the vented plunger and out of the syringe by the systolic pressure of the incoming blood. These vented plunger syringes are used not only for the collection of the sample but are also used for transporting the collected sample to the laboratory. For accurate analysis of the gas contents of the blood sample, it is important that all air-bubbles be expelled from the syringe.

Currently known vented plungers generally function in the following manner: they are slidably positioned within the syringe body to variate the capacity of the chamber in the syringe body to the desired volume, and they incorporate an automatic-closing air vent, by means of an air-permeable porous material positioned in the plunger, said porous material having microscopic pores which allows the air in the syringe to flow out of the syringe body until the material becomes wet from the incoming blood sample. These porous materials which permit air to pass through, but do not allow liquids to pass through, are well known in the art. It is important to note that after these porous materials become wet, they no longer permit air to pass through the porous material.

Additionally, some vented plungers include the feature of being able to alternatively aspirate the blood into the syringe. This aspirating feature is generally accomplished by some digital means or a plug which fits over the hole at the end of the plunger stem to close off the reverse flow of air through such hole into the chamber of the syringe. Thus, as an alternative, when difficulties are experienced in getting the blood to fill the chamber of the syringe freely under its own pressure, the vented plunger can be manually retracted to help aspirate the blood into the syringe.

There are some problems with currently known vented plungers. As examples, some have limited venting surface area, such as only three small vent holes across the entire front face of the plunger. Consequently, if the syringe is not held such that at least one vent hole is at the top position on the periphery of the plunger tip, air-bubbles may be trapped in the syringe. Some vented plungers have insufficient venting surface which restricts the volume of air flow, thereby resulting in longer fill times and greater patient trauma and discomfort. Other vented plungers have utilized a thin, film membrane of a porous material providing greater venting surface area, but which may occasionally rupture from the pressure or from the vacuum forces which are developed when the plunger is pushed in and out prior to use. Other vented plungers have tortuous, indirect air paths from the blood collecting chamber to the air-permeable material which can trap air-bubbles.

There are also vented plungers which have the air-permeable material positioned in close proximity to the front end of the plunger. Since the blood is pulsating into the syringe body, this can result in the blood splashing onto the surface of this material and closing of the air-permeable character of the material before all the air has been expelled. The fact that the syringes may not be held in a vertical position while the blood sample is being collected, but are held at a 45 degree or less oblique angle, further increases the possibility of splashing blood sealing the surface of the air-permeable material prematurely.

Another problem is that as the blood enters into the syringe, the head of that column of blood comes in contact with any air in the syringe. This makes the blood sample subject to artificial oxygenation which can cause erroneous readings on the blood sample. This condition is compounded by the pulsating wave action of the incoming blood, causing turbulent mixing of the air into the blood. When this small portion of oxygenated blood is allowed to mix with the main portion of the blood sample that is to be used for analysis, test determinations can be altered.

Other problems include the inability to see exactly when the the filling process has been completed so that the needle can be expeditiously removed from the patient. Also, the inability to visually ascertain that all air bubbles have been expelled in an inherent deficiency in some designs of the prior art. Consequently, the inability to see any air bubbles may give the operator a false sense of security. Such air bubbles which cannot be seen may remain in the syringe and may distort test determinations. The capability to precisely and accurately ascertain when the filling process has been completed and that all air bubbles have been expelled is essential to the quality of the sample to provide meaningful test determinations and to the well being of the patient.

SUMMARY OF THE PRESENT INVENTION

The present invention is a plunger barrel with sealing means on one end forming a first blood receiving chamber within a syringe body and fingergrip means on the opposite end which is slidably insertable into the body of a syringe to variate the volume capacity of the chamber of said syringe body in response to the systolic blood pressure and which has a capillary action view-tube within the plunger stem of a smaller diameter than the inside diameter of the syringe body, said capillary action view-tube being positioned in constant sealing contact with the said sealing means and in communication with the said chamber and extending longitudinally towards said fingergrip end of said plunger within said plunger barrel. The view-tube further has an air-permeable, liquid impermeable porous material positioned in the portion of the view-tube which is nearest the said fingergrip end of the plunger barrel.

In an alternative embodiment, the present invention may also provide a secondary chamber area in the plunger which is separated from the first chamber of the syringe body by a passageway of reduced diameter.

BRIEF DESCRIPTION OF THE DRAWINGS

The present invention is its basic inventive concept and alternative embodiments is disclosed in the illustrative accompanying drawings which are to be understood as non-restrictive in the application of the invention.

FIG. 1 is an exploded perspective view of the basic concept of the present invention.

FIG. 2 is a cross-sectional longitudinal axis view of the invention shown in FIG. 1.

FIG. 3 is a cross-sectional view of the basic present invention along the plane 3—3 in FIG. 2.

FIG. 4 is a cross-sectional view of a first alternate embodiment of the present invention.

FIG. 5 is a cross-sectional view of the alternate embodiment of the present invention along the plane 5—5 of FIG. 4.

FIG. 6 is a cross-sectional view of the alternate embodiment of the present invention along the plane 6—6 in FIG. 4.

FIG. 7 is a partial cross-sectional view of the second alternative embodiment of the present invention.

FIG. 8 is a cross-sectional view of a third embodiment of the present invention.

FIG. 9 is a cross-sectional axial view of a fourth embodiment of the present invention.

FIG. 10 is a cross-sectional axial view of a fifth embodiment of the present invention.

FIG. 11 is a partial cross-sectional axial view of the present invention in all of its embodiments shown inserted into a syringe as disclosed in U.S. Pat. No. 4,320,770.

DETAILED DESCRIPTION OF THE PRESENT INVENTION

With reference to FIGS. 1-3, the basic concept of the present invention can be seen to comprise a plunger stem 10 which, in turn, comprises a transparent barrel 11 which is a hollow cylindrical tube having a finger grip end 12 with opening 12a and an opposing end 13 with an apertured opening 14. The opposing end 13 has secured thereto a sealing means 15 of resilient composition. Contained within the sealing means 15 and extending inwardly of said barrel through said apertured opening 14 is a cylindrical capillary action view tube 16 having a view-through transparency for observation of any fluid therein. The cylindrical tube 16 contains at a spaced distance from its said juncture with said sealing means a plug 19 of an air-permeable, liquid impermeable material. The disk-like base 17, seen in FIGS. 1 and 2, is fitted in a matching annular recess 18 in sealing means 15 and abuts a cylindrical extension 20 surrounding the apertured opening 14 of barrel 11. Sealing means 15 comprises a circular, primary and very flexible sealing bead 21 having a conical inwardly extending interior surface 22 which forms the primary chamber 22a with an opening 20a axially mating with the cylindrical tube 16 for receipt of blood from a patient. Spaced rearwardly from the primary sealing bead 21 and circumferentially surrounding the forward extension 20 of the tube 16 is a second sealing bead 23 integral with sealing means 15. While bead 23 is shown as an arcuately contured ring, it may have a knife-like terminus.

Refering now to FIG. 4-6, an alternative plunger 24 of the present invention is shown in a syringe body 25 which is seen in phantom lines forming the blood receiving chamber 25a, the plunger 24 comprises a hollow transparent cylindrical barrel stem 24a having a markedly reduced diameter, as contrasted with barrel stem 10 in FIGS. 1-3, forming a capillary viewing tube 33 terminating at its exterior end in the same conventional finger grip portion 26 as fingergrip 12 in FIG. 2 and terminating at its interior end in a sealing means 15 substantially identical to that shown in FIGS. 1 and 2. The barrel stem 24a seen in FIGS. 4 and 5 differs from the barrel stem 11 in FIGS. 1 and 2 in that, to support the barrel stem 24a within the syringe body 25, the portion of the barrel stem 24a extending outwardly from sealing means 15 carries four radially extending arms 27, 28, 29 and 30, which terminate in disk 31 from which barrel stem 24a extends outwardly to fingergrip 26. Within barrel stem 24a there is a plug 32 of air-permeable, liquid-impermeable material. As seen in FIG. 4, the interior cylindrical channel 33 of barrel stem 24a can be closed off at the exit opening 34 by selectively using a plug 35, seen in phantom lines, or by the placement of a finger 36, shown in phantom lines, if it becomes necessary to provide manual aspiration, i.e., drawing the plunger barrel stem 24a outwardly of syringe 25 to increase the flow of blood from the patient.

Referring now to FIG. 7, there is shown a tubular plunger barrel 11a, substantially identical to that in FIGS. 1 and 2, containing at its interior end face 37 a sealing means 38 having a single sealing bead 39 of a more or less knife-like edge providing a conical blood receiving chamber 40. In lieu of the axially outwardly extending portion 16 or 24a, as seen in FIGS. 2 and 4, there is a cylindrical hollow, closed end tube 41 forming the capillary action tube 43, which is of an air-permeable, liquid impermeable material securely held within cylindrical recess 42 of the interior end 42a of barrel 11a which mates with aperture 42b in blood receiving chamber 40.

With reference to FIG. 8, there is shown a plunger 44 having a hollow barrel 44a similar to barrel 24a in FIG. 4 and sealing means 45 generally similar to that in FIGS. 2 & 4 and four extending arms 46 and 47 (extending arms 48 and 49 not being visible but substantially identical to arms 28 & 30 in FIG. 5). The sealing means 45 provides a first receiving chamber 50. Barrel 44a has an axial interior channel 51 forming a capillary action view tube which decreasingly tapers from first chamber 50 to a secondary cylindrical chamber 52 which terminates in a cylindrical fingergrip disk 53. Within chamber 52 is a plug 52a of air-permeable, liquid impermeable material.

In FIG. 9 there is shown a plunger 54 incorporating the basic concept of the present invention in which the plunger has a hollow cylindrical barrel stem 54a having an equally cylindrical bore 55 terminating at its outer end in a hollow finger grip 56 and a sealing means 57 received by recess 54b in the interior end 54c of barrel 54a with a single very flexible sealing lip 58 forming blood receiving chamber 58a. Barrel 54a has on the portion of its surface extending outwardly of sealing means 57 four radially extending ribs 59-61, (ribs 60 & 62 not seen). Barrel 54a contains within bore 55, at a distance between the outward ends of ribs 59-62 a plug 63 of an air-permeable liquid impermeable material.

In FIG. 10 there is seen a hollow cylindrical plunger 70 having a barrel stem 71 of a reduced cylindrical diameter similar to the barrel stem of the plungers seen in FIGS. 4, 8 and 9. Barrel 71 contains a hollow cylindrical passageway 72 which terminates at its outer end in a hollow finger grip 73. The barrel 71 carries the four radially extending arms 74–77 (arms 75 & 77 not visible) as previously described with reference to FIG. 5. Positioned between the exterior ends of arms 74–77 and finger grip 73 is plug 78 of an air-permeable, liquid impervious material substantially identical to plugs 19, 32, 52a, 63, 78 and 93. The interior end of barrel 71 carries a sealing means 80 which is substantially identical to sealing means 15 and 45, in that it has a first sealing bead 81 and a barrel supported secondary sealing bead 82 secured within recess 83 in the interior end portion of barrel 71. The interior end of plunger 70 differs from that shown in FIGS. 2, 4 and 8 in that it is formed as a basically cylindrical unit 84 in which its interior portion comprises an interiorly extending conical recess 85 forming a first blood receiving chamber 85a and having an opening 86 of reduced size which communicates with passageway 72, creating in essence a second chamber as in FIG. 8.

FIG. 11 shows a sealable syringe body 90 with attached catheter 91, but more particularly a sealable syringe body such as disclosed in U.S. Pat. No. 4,320,770, as compared to the standard syringe barrel 25 shown in phantom in FIG. 4. The sealable syringe body 90 forms the first blood receiving chamber 90a. The plunger 92 is one of those shown in FIGS. 4, 8, 9 or 10. It can be seen in this embodiment that it is similar to FIGS. 8, 9 and 10 in that the view tube area adjacent the plug 93 would be visible outside the body of the syringe; wherein in the the embodiments of FIGS. 1, 2 and 4 the view tube area adjacent the plug would have to be viewed through the transparent syringe barrel.

The present invention is a vented plunger which provides a solution to all of the aforementioned problems in a manner heretofore unknown. The present invention provides venting capability across the entire front face of the plunger. The present invention provides a non-rupturable porous material of adequate surface area for effective expulsion of the air in the syringe. Use of the plungers 10, 24, 44, 54, and 70 provides the capability to, alternatively, aspirate the blood sample into the syringe. It is important to understand that the band-like sealing means 15, 38, 45, 57 and 80 at the end of the barrel stems 11, 24a, 44a 54a and 71 are in constant sealing relationship with the barrel stems. The operator can close off air passage through the plunger and subsequently into the syringe by placing a finger over the hole 12a, 34, 53a, 56a and 73a at the end of the cylindrical plunger stem. It can be readily seen that a stopper could be utilized to plug the hole in a similar manner.

The present invention provides a novel capillary action view-tube 16, 33, 51, 55 and 72 between the primary chambers 22a, 25a, 50, 58a or 85a of the syringe and the porous material 19, 32, 52a, 63, and 78. The capillary action view-tube and the hollow stem will, by the distance that is created between the chamber of the syringe body and the location of the porous material and the stablizing action upon the pulsating turbulent flow of the incoming blood, reduce the possibility of the porous material becoming wet from the pulsating blood before all the air-bubbles have been expelled. Additionally, the area directly adjacent the porous material, will be clearly visible. This visibility will let the operator know precisely the moment the syringe body has finished filling and if all the air-bubbles have been effectively expelled. As may occasionally happen with all arterial blood gas syringes, if all the air-bubbles have not been expelled, the operator can take appropriate steps to manually expell them. It would be agreed to by many that air-bubbles may be inherent to this procedure. Many venting plungers of the prior art, by their own design, make it difficult to see retained air-bubbles. The present invention was developed with the concept that it is preferable for the operator to see the air-bubbles and deal with them accordingly, rather than not to be able to see them and possibly compromise the accuracy and meaningfulness of the test results.

Further, the stabilizing action of the capillary view-tube will serve to baffle the pulsating wave action of the incoming blood, thereby reducing the mixing of air into the blood sample. The small portion of blood that may have experienced oxygenation by the air within the syringe body will be in the capillary action tube area, separated away from the main portion of blood which will be utilized for anaylsis. It is a requirement of arterial blood gas samples that they be transported to the lab for analysis as quickly as possible. Therefore, diffusion of the oxygen in the small oxygenated portion into the major sample portion is further minimized or totally eliminated.

In an embodiment shown in FIG. 8, the plunger may provide a secondary chamber 52 in the plunger, which is separated from the primary or first chamber 50 of the syringe by an elongated reduced diameter passageway 51, and in which secondary chamber 52 there is positioned an air-permeable, liquid impermeable porous material 52a. This secondary chamber 52 may provide additional space for oxygenated blood and air-bubbles in an area which would be further separated from the main blood sample. Also, this reduced diameter passageway 51 would serve to further baffle the fluid flow and to separate the columns of blood.

In the embodiment in FIG. 7, the capillary action tube 41 of an air-permeable, liquid impermeable porous material would provide venting capability through all the tubular wall surfaces, as well as through the end of the tube. This additional venting surface would minimize the possibility of air-bubbles getting trapped within the tube.

The use of a sealing means with a single sealing bead 39 as shown in FIG. 7 and 58 in FIG. 9 which have minimal drag resistance and can be carried by plungers 10, 24, 11a, 44, 54 and 70 in FIGS. 2, 4, 7, 8, 9 and 10 could be utilized in conjunction with a novel method for collecting arterial blood gas samples which is described as follows:

Instead of pre-setting the plunger within the syringe body to the desired volume capacity, the plunger would be set at the full-forward minimum capacity position, The arterial puncture would be accomplished in the usual manner, and as the blood entered into the syringe under its own systolic pressure, all the air in the syringe would be forced out until the porous material became wet from the incoming blood;

At this point, the systolic pressure of the blood will start driving the plunger rearwardly until the operator stops the plunger at the desired volume, or until the plunger hits a pre-determined mechanical stop.

The arterial puncture is terminated and the collected sample is treated in the usual manner.

The advantages of this novel specimen collection method include:

When standard vented syringe plungers are pre-set for a volume capacity of 3 cc's, and for whatever reasons such as collasped arteries, low blood pressure or difficulties in finding the artery with the needle, the actual collected sample is only 1 to 2 cc, there will of course be 1 or 2 cc of air remaining in the syringe. Typically, if the operator continues to try to obtain a greater amount of sample by aspirating the blood into the syringe, first, the incoming blood may become mixed with the air that is in the syringe; secondly, the decompression (vacuum) force of that aspiration may alter the oxygen tension of the blood sample; and thirdly, that remaining air is further mixed into the sample when the operator takes action to manually expell the air.

With the light drag embodiment of the present vented plunger, when it is pre-set at its forwardmost position, the volume capacity and therefore the initial amount of air in the syringe will be minimal. In a normal collection operation, wherein the full amount of sample is collected, after the initial small portion of blood voids the syringe of all air, the major portion of the blood that will be utilized for test purposes, will be filling into a syringe that is free of air. In such situations that a sample volume shortfall occurs, aspiration of the remainder of the sample may also be accomplished with no air in the syringe. Under any circumstances, there is less air in the syringe and less chance of unwanted oxygenation of the blood sample with this combination venting and light drag plunger method.

The present invention may be summarized as a plunger used in a syringe body for blood gas collection in which the plunger contains a transparent, viewing chamber having an air-permeable, blood or liquid impervious plug positioned near its exterior end and sealing means on the interior of said plunger which prevent the escape of the blood around or through its periphery, while in some of its embodiments, eliminating or substantially reducing the resistance to rearward movement of the plunger by the systolic pressure of the blood. Those of skill in the related art will recognize that the changes in the exterior form or shape of the plunger barrel will come within the scope of the present invention as recited in the following claims.

What is claimed is:

1. A venting, automatic-stopping, aspirating plunger for syringes used in collection of blood, comprising:
   an elongated hollow plunger barrel stem with band-like sealing means on its interior end within the syringe body forming a chamber communicating with said hollow stem and a fingergrip means on the exterior end and being slidably insertable into the body of a syringe to variate the volume capacity of the said chamber of said syringe while maintaining a sealing relationship between said sealing means of the plunger and internal surfaces of the syringe body;
   a hollow capillary action view-tube formed within the said hollow plunger barrel stem, said capillary action view-tube positioned in constant sealing contact with the said band-like sealing means and extending co-axially with the longitudinal axis of said stem towards said fingergrip end of said plunger, and;
   an air-permeable porous material positioned in the said hollow capillary action view-tube nearest said fingergrip end of the plunger, said porous material characterized as having microscopic pores within for permitting air to permeate therethrough but which will not permit the passage of blood.

2. The apparatus according to claim 1, wherein the said band-like sealing means has two axially spaced annular sealing beads making said sealing relationship.

3. The apparatus according to claim 1, wherein the said band-like sealing means has only one annular sealing bead making said sealing relationship to provide minimized frictional drag thereby requiring less force to slide the said plunger within the said syringe barrel.

4. The apparatus according to claim 1, wherein the said capillary action view-tube is in direct open communication with the said chamber of said syringe.

5. The apparatus according to claim 1, wherein there is a passageway of reduced diameter positioned between the said chamber of said syringe to a secondary chamber in the said hollow plunger stem, said secondary chamber containing said air-permeable porous material and being adjacent said grip means, said secondary chamber having an interior diameter greater than the diameter of said passageway.

6. A venting, automatic-stopping, aspirating plunger for syringes, comprising:
   a hollow plunger barrel stem with band-like sealing means secured in a annular recess on one end and fingergrip means on the opposite end, said sealing means forming with said one end of said stem an interiorly extending conical chamber, said stem being slidably insertable into the body of a syringe to variate the volume capacity of said syringe while maintaining a sealing relationship between the peripheral surfaces of the sealing means and the internal surfaces of the syringe barrel, said chamber having an aperture in said one end of said stem, and;
   a capillary action tube within the said hollow plunger barrel stem, said capillary action tube being formed entirely of an air-permeable porous material and positioned in constant sealing contact with a recess in the interior end of the said plunger barrel and the said band-like sealing means in communication with siad aperture and extending axially of said barrel from said chamber towards said fingergrip end of said plunger; said porous material characterized as being comprised of microscopic pores for permitting air to permeate therethrough but which will not permit the passage of blood.

7. Method for the collecting of an arterial blood sample for blood gas analysis into a hypodermic syringe body which has been pre-heparinized with a dry form of anti-coagulant and in which syringe body there is a hollow barrel-like plunger inserted into the barrel of said syringe for variating the volume capacity of said syringe, wherein said plunger incorporates a sealing means on its interior end within said syringe body which has at least one annular sealing bead establishing sealing relationship between the external peripheral surfaces of said sealing means and internal surfaces of the syringe body, thereby eliminating or substantially reducing the frictional drag and minimizing the amount of force required to move the said plunger within the said syringe body; the said sealing means forming an interiorly extending conical chamber to receive said sample, the said plunger further having a tube within said plunger barrel in communication with said chamber and extending outwardly toward the exterior end of said plunger with an air-permeable porous material within said tube which allows the venting of air into and out of the said hollow plunger barrel but which material does not allow the passage of blood, comprising the steps of pre-setting the said plunger at its full forward minimum capacity position; placing the said syringe in communication with a source of blood from which the said sample is to be taken; permitting the systolic pressure of the blood to fill the said syringe with said blood sample and forcing the air which was in the said chamber of said syringe body out through the said porous material; continuing to fill the said syringe body with the said blood sample by the said systolic pressure thereby pushing the said plunger rearwardly until the desired volume of blood sample is collected, and removing the said syringe with collected said arterial blood sample away from the said source of blood.

8. The method according to claim 7 wherein the flow of blood into the syringe body is terminated by visual sighting of the pre-determined quantity.

9. The method according to claim 7 wherein the flow of blood into the syringe body is terminated by the plunger barrel contacting a pre-determined stop.

10. An arterial blood gas sample collecting device comprising in combination an elongated self-sealing syringe and a venting, automatic-stopping, aspirating plunger wherein said syringe comprises:

a hollow, cylindrical body having an open end and an opposing end with an aperture therethrough eccentrically positioned with reference to the longitudinal axis of the body, a rotatable sealing cap for said closed end, said cap having a depending skirt encompassing the closed end of said body with means on said cap engaging means on the external surface of said syringe body to limit rotational movement of said cap which has an aperture in its external end extending therethrough parallel to the longitudinal axis of said cap, which aperture has an eccentricity relative to said axis substantially identical to the eccentricity of the aperture in said closed end, said closed end of said syringe body having an O-ring seal around said closed end aperture extending above said closed end outer surface into contact with an inner surface of said cap and providing a sealed bearing surface for said cap during rotation thereof between a position when both of said apertures are in communication and a position in which said apertures are not in communication;

wherein said plunger comprises:

an elongated hollow plunger barrel stem with band-like sealing means on its interior end within said syringe body forming a chamber communicating with said hollow stem and fingergrip means on the exterior end and being slidably insertable into the body of a syringe to variate the volume capacity of the chamber of said syringe while maintaining a sealing relationship between said sealing means of the plunger and internal surfaces of the syringe body;

a hollow capillary action view-tube formed within the said hollow plunger barrel stem, said capillary action view-tube positioned in constant sealing contact with the sand band-like sealing means and extending co-axially with the longitudinal axis of said stem towards said fingergrip end of said plunger, and;

an air-permeable porous material positioned in the said hollow capillary action view-tube nearest the said fingergrip end of the plunger, said porous material characterized as having microscopic pores within for permitting air to permeate therethrough but which will not permit the passage of blood.

11. The apparatus according to claim 10, wherein the said band-like sealing means has two axially spaced annular sealing beads making said sealing relationship.

12. The apparatus according to claim 10, wherein the said band-like sealing means has only one annular sealing bead making said sealing relationship to provide minimized frictional drag thereby requiring less force to slide the said plunger within the said syring barrel.

13. The apparatus according to claim 10, wherein the said capillary action view-tube is in direct open communication with the said chamber of said syringe.

14. The apparatus according to claim 10, wherein there is a passageway of reduced diameter positioned between the said chamber of said syringe to a secondary chamber in the said hollow plunger stem, said secondary chamber containing said air-permeable porous material and being adjacent said grip means, said secondary chamber having an interior diameter greater than the diameter of said passageway.

15. The apparatus according to claim 10 wherein said plunger comprises:

a hollow plunger barrel stem with band-like sealing means secured in a annular recess on one end and fingergrip means on the opposite end, said sealing means forming with said one end of said stem an interiorly extending conical chamber and being slidably insertable into the body of a syringe to variate the volume capacity of said syringe while maintaining a sealing relationship between the peripheral surfaces of the sealing means and the internal surfaces of the syringe barrel, said chamber having an sperture in said one end of said stem, and;

a capillary action tube within the said hollow plunger stem, said capillary action tube being formed entirely of an air-permeable porous material and positioned in constant sealing contact with a recess in the interior end of the said plunger barrel and the said band-like sealing means in communication with said aperture and extending axially of said barrel from said chamber towards said fingergrip end of said plunger; said porous material characterized as being comprised of microscopic bores for permitting air to permeate therethrough but which will not permit the passage of blood.

* * * * *